(12) United States Patent
Kirste et al.

(10) Patent No.: US 10,571,464 B2
(45) Date of Patent: Feb. 25, 2020

(54) DETECTING AN ANALYTE AND DETERMINING THE CONCENTRATION OF AN ANALYTE USING MAGNETIZABLE BEADS

(71) Applicant: Orgentec Diagnostika GmbH, Mainz (DE)

(72) Inventors: Vinzenz Kirste, Zornheim (DE); Wigbert Berg, Mainz (DE); Vukic Soskic, Mainz (DE)

(73) Assignee: Orgentec Diagnostika GmbH, Mainz (DE)

( * ) Notice: Subject to any disclaimer, the term of this patent is extended or adjusted under 35 U.S.C. 154(b) by 762 days.

(21) Appl. No.: 14/433,981

(22) PCT Filed: Oct. 9, 2013

(86) PCT No.: PCT/EP2013/071066
§ 371 (c)(1),
(2) Date: Apr. 7, 2015

(87) PCT Pub. No.: WO2014/056987
PCT Pub. Date: Apr. 17, 2014

(65) Prior Publication Data
US 2015/0241422 A1    Aug. 27, 2015

(30) Foreign Application Priority Data

Oct. 11, 2012 (EP) .................................... 12188204
Nov. 13, 2012 (EP) .................................... 12192353

(51) Int. Cl.
*G01N 33/543* (2006.01)
*G01N 27/74* (2006.01)

(52) U.S. Cl.
CPC ..... *G01N 33/54333* (2013.01); *G01N 27/745* (2013.01)

(58) Field of Classification Search
CPC ......... G01R 33/1269; G01N 33/54333; G01N 27/745
See application file for complete search history.

(56) References Cited

U.S. PATENT DOCUMENTS

| 5,145,784 A * | 9/1992 | Cox ................. G01N 33/54333 436/523 |
| 5,374,531 A * | 12/1994 | Jensen ............. G01N 33/56966 435/7.24 |
| 6,294,342 B1 | 9/2001 | Rohr et al. |
| 10,002,483 B2 * | 6/2018 | Sandhu ..................... B44F 1/10 |
| 2009/0065359 A1 * | 3/2009 | Zhou ....................... B82Y 25/00 204/556 |
| 2009/0104707 A1 * | 4/2009 | Wang ............... G01N 33/54326 436/86 |
| 2009/0311733 A1 * | 12/2009 | Korpela .................... B03C 1/01 435/29 |
| 2010/0330698 A1 * | 12/2010 | Evers ...................... B82Y 25/00 436/501 |
| 2011/0151569 A1 * | 6/2011 | Rowell .................... G01N 1/40 436/86 |
| 2011/0223612 A1 * | 9/2011 | Wang ................... G01N 27/745 435/7.1 |
| 2012/0164634 A1 * | 6/2012 | Heinrich .......... G01N 33/54333 435/6.1 |
| 2016/0041153 A1 * | 2/2016 | Brown ............... G01N 33/5308 435/7.23 |

OTHER PUBLICATIONS

Rapoport et al., "Integrated Capture, Transport, and Magneto-Mechanical Resonant Sensing of Superparamagnetic Microbeads Using Magnetic Domain Walls," Lab Chip, 2012, 12:4433-4440.
Weber et al., "Magnet-Guided Transduction of Mammalian Cells and Mice Using Engineered Magnetic Lentiviral Particles," Journal of Biotechnology, 2009, 141:118-122.
PCT International Search Report for PCT Application No. PCT/EP2013/071066 dated Jan. 16, 2014 (6 pages).

* cited by examiner

*Primary Examiner* — Ann Y Lam
(74) *Attorney, Agent, or Firm* — Eversheds Sutherland (US) LLP

(57) ABSTRACT

The invention relates to methods, reagents and devices for detecting an analyte in a sample.

8 Claims, 21 Drawing Sheets

DETECTING AN ANALYTE AND DETERMINING THE CONCENTRATION OF AN ANALYTE USING MAGNETIZABLE BEADS

CROSS REFERENCE TO RELATED APPLICATIONS

This application claims the priority benefit of PCT/EP2013/071066 filed on Oct. 9, 2013 and European Application Nos. 12188204.7 and 12192353.6 filed on Oct. 11, 2012 and Nov. 12, 2012, respectively. The contents of these applications are hereby incorporated by reference in their entirety.

DESCRIPTION

Figure 1:
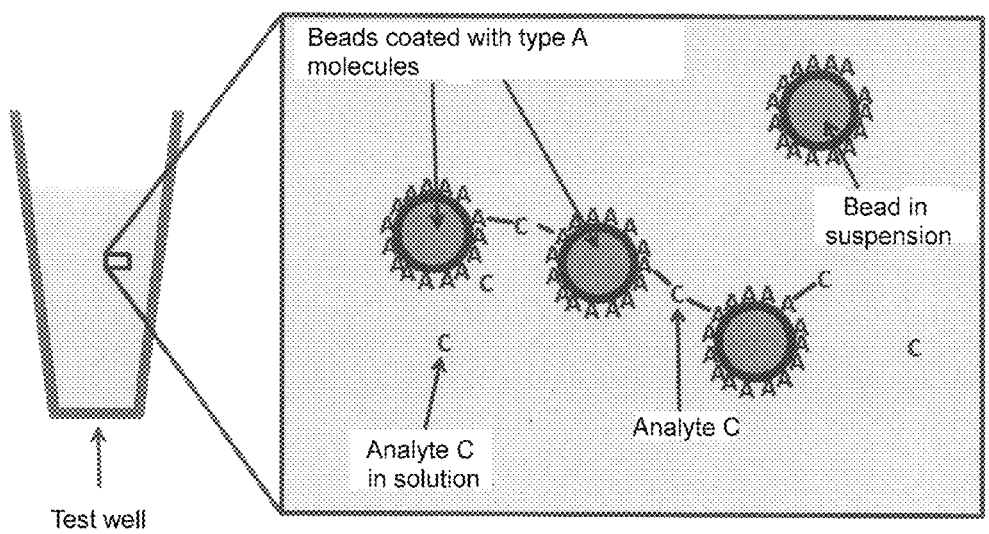
FIG. 1 illustrates a test format for detecting an analyte (C) having a plurality of binding sites for a binding molecule (A).

The invention relates to methods, reagents and devices for detecting an analyte in a sample.

In order to detect analytes, for example clinical parameters for medical diagnosis, there are many different methods in which the presence and/or concentration of the analyte in a sample is/are determined by means of appropriate methods, in particular optical and/or electrochemical methods.

The problem addressed by the invention is that of providing a novel and simple method for detecting analytes and of providing reagents and systems suitable for said method.

In the present invention, the presence and/or concentration of an analyte to be detected is determined by means of magnetisable beads, the beads being coated with binding molecules which can aggregate or cross-link depending on the presence and/or concentration of the analyte in the sample. The level of this aggregation or cross-linkage is detected magnetically, whereby an analyte present in the sample can be qualitatively and/or quantitatively determined.

A first aspect of the invention relates to a method for detecting an analyte in a sample, comprising the following steps:

(a) bringing the sample into contact with magnetisable beads, the beads being coated with binding molecules so that the magnetisable beads aggregate depending on the presence and/or concentration of the analyte in the sample, and (b) determining the degree of aggregation of the magnetisable beads by magnetic detection.

Another aspect of the invention relates to a reagent for detecting an analyte in a sample, comprising one or more species of magnetisable beads, the beads being coated with binding molecules so that the magnetisable beads can aggregate depending on the presence and/or concentration of the analyte in the sample.

The reagent can be used in a method for magnetically detecting an analyte, in particular in a method as described above.

An additional aspect of the invention is a device for detecting an analyte in a sample, comprising
(a) a test well,
(b) a magnet for generating a magnetic field in the test well, and
(c) a magnetic sensor for measuring changes over time in the magnetic field in the test well.

The device can be used in a method for magnetically detecting an analyte, in particular in a method as described above.

The invention relates to detecting an analyte in a sample. In principle, the analyte can be any substance that can be detected by binding to one or more specific binding partners. For example, the analyte is a protein, e.g. an antibody, a receptor, a receptor ligand, an enzyme etc., a nucleic acid, e.g. a piece of DNA or RNA, a hormone, a signal transmitter, a metabolite, a medicine, a drug or a pathogen, such as a virus or bacterium, or any other type of detectable substance. Preferably, the method is used for detecting antibodies, for example antibodies against pathogens, autoimmune antigens, metabolites, etc.

The sample is preferably of biological origin, e.g. a bodily fluid sample, such as blood, serum, plasma, urine, saliva, liquor, etc., a tissue sample, a cell culture sample, a forensic sample, an environmental sample, etc.

According to the present invention, magnetisable beads are used and are preferably magnetisable nanobeads. The size of the beads is preferably in the range of from 1-10000 nm, more preferably from 5-1000 nm, and most preferably from 10-100 nm. The beads can be magnetised. Preferably, the beads are paramagnetic and/or superparamagnetic beads. They can for example consist of or contain cobalt. Other possible materials are iron or iron oxide (e.g. magnetite or iron alloys). In a preferred embodiment, the beads are paramagnetic and/or superparamagnetic beads consisting of or containing magnetite. Polymer beads containing magnetite particles have proven to be particularly advantageous. Advantageously, beads having a high saturation magnetisation, e.g. of from 1-200 emu/g, preferably from 2-70 emu/g or from 50-200 emu/g, are used in order to generate a signal to be detected that is as strong as possible.

The beads are coated with binding molecules so that the beads cross-link or aggregate depending on the presence and/or concentration of the analyte.

In certain embodiments, use is made of binding molecules which represent specific binding partners of the analyte, i.e. interact with the analyte in a specific manner, e.g. via an antibody-antigen bond, a receptor-ligand bond or via a nucleic acid hybridisation. If, for example, the analyte is an antibody, the beads used for detection can be coated with an antigen which is recognised by the antibody. If, on the other hand, the analyte is an antigen, the beads can be coated with an antibody or antibody fragment directed against the antigen. If the analyte is a nucleic acid, the beads can be coated with nucleic acids (or nucleic acid analogues) which are complementary to the analyte.

In other embodiments, use can be made of binding molecules which indirectly, i.e. via a non-immobilised binding partner, bind specifically with the analyte. In this way, "universal" binding molecules, e.g. antibodies directed against the constant domain of antibodies of a certain species (e.g. mouse, rat, etc.), can be immobilised on the beads. Non-immobilised antibodies for these particular species are then used as detection antibodies which can bind specifically with the analyte.

In an additional embodiment, the beads can also be coated with either the analyte itself or an analogue of the analyte, e.g. for use in a competitive test.

For the present invention, it is possible to use one single species of beads, i.e. one single type of beads coated with one binding molecule, or a plurality of species of beads, i.e. a plurality of types of beads coated with different binding molecules.

In addition, non-immobilised binding molecules can also be added to the test batch, e.g. non-immobilised binding partners for the analyte, or connecting molecules between beads that compete with the binding of the analyte to the beads.

The beads can be coated with binding molecules by means of known methods, e.g. by adsorption, covalent bonding, e.g. using chemical coupling reagents, and/or by high-affinity interactions, e.g. via a biotin-streptavidin bond.

In certain embodiments, it may be preferable to provide the beads with a base coat, preferably a hydrophilic base coat, so as to reduce non-specific self-aggregation as a result of hydrophobic and/or magnetic interactions. In other embodiments, use can also be made of the non-specific aggregation effect to determine the concentration of the analyte.

In the following, various embodiments of test formats will be described in more detail. A first embodiment relates to detecting an analyte having a plurality of binding sites for a binding molecule, for example detecting an antibody. This embodiment is shown in FIG. 1. If type C molecules (analyte) have a plurality of binding sites for type A molecules (binding molecule), the method proceeds as follows: Beads are coated with type A molecules. Preferably, a homogenous bead suspension is then produced. Next, the beads and a sample fluid, which contains the analyte C at a concentration c to be detected, are introduced into a test well. The type C molecules bind to the type A molecules on the surface of the beads. Since the analyte C contains a plurality of binding sites for A, the beads aggregate. The higher the concentration c of the analyte C, the greater the degree of aggregation of the beads.

Figure 2:
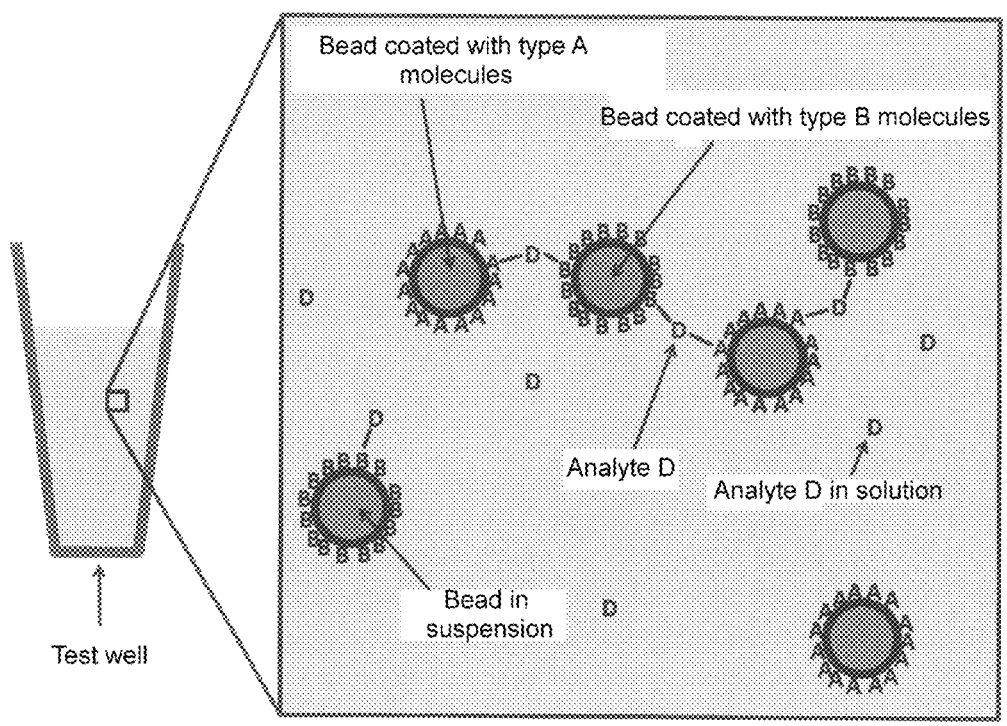
FIG. 2 illustrates a test format for the determination of an analyte (D) having one or more binding sites for type A molecules and one or more binding sites for type B molecules using beads coated with type A molecules and others coated with type B molecules.

In another embodiment, use is made of a test format which allows for the determination of an analyte having binding sites for two different binding molecules. This embodiment is shown in FIG. 2. If type D molecules (analyte) have one or more binding sites for type A binding molecules and one or more binding sites for type B binding molecules, some of the beads are coated with type A molecules (="type A beads") and others are coated with type B molecules (="type B beads"). Preferably, a homogenous bead suspension containing type A and type B beads is first produced. The concentrations of the two bead types have already been optimised beforehand in terms of binding affinities between A and D and between B and D. The beads and a sample fluid, which contains the analyte D at a concentration c to be detected, are then introduced into a test well. The type D molecules bind to type A molecules on the surface of the type A beads and bind to type B molecules on the surface of the type B beads, whereby the beads cross-link or aggregate. The higher the concentration c of the analyte D, the greater the degree of aggregation.

Figure 3:
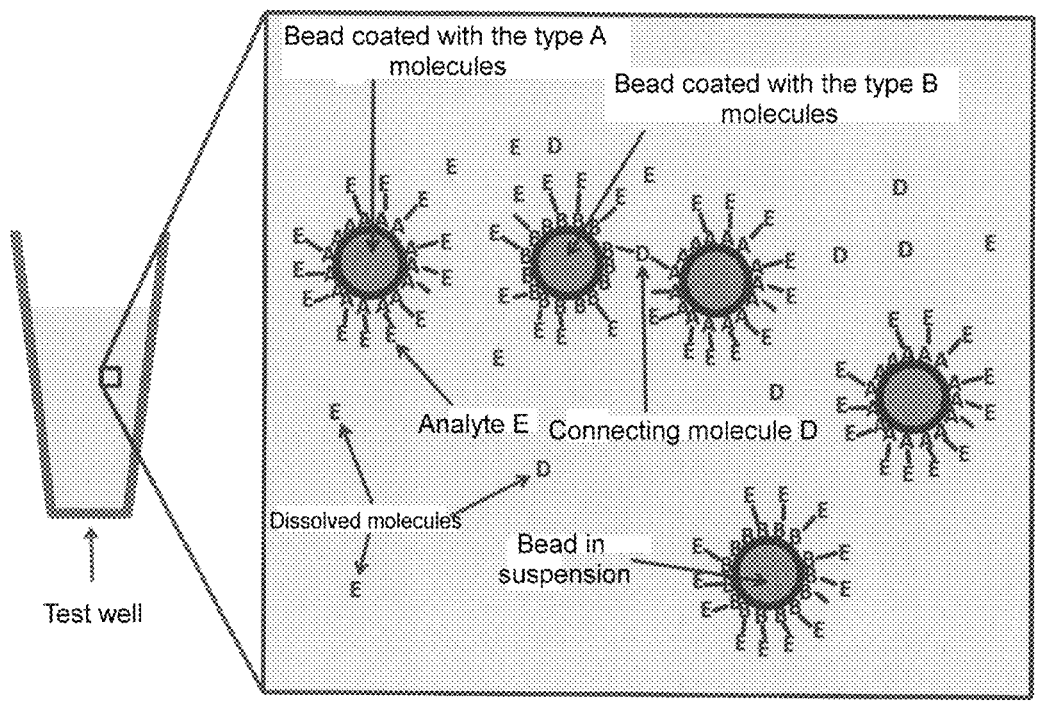
FIG. 3 illustrates a test format wherein binding of the analyte (E) to type A or type B binding molecules immobilized on beads inhibits bead aggregation because there are fewer free binding sites for type D connecting molecules.

An additional embodiment of the invention comprises inhibiting the formation of aggregates when the analyte to be detected is present in the sample. This embodiment is shown in FIG. 3. Type E molecules (analyte) have one or more binding sites for type A binding molecules and one or more binding sites for type B binding molecules, wherein, if there is more than one binding site, binding of E to A inhibits the formation of a bond of E to B, and the formation of a bond between E and B inhibits the formation of a bond of E to A. Some of the beads used in this embodiment are coated with type A molecules and others are coated with type B molecules. Preferably, a homogenous bead suspension containing type A and type B beads is first produced, the concentrations of the two bead types advantageously having been optimised beforehand as described above. The beads and a sample fluid, which contains the analyte E at a concentration c to be detected, are then introduced into a test well. In the absence of the connecting molecule D, the beads do not cross-link or aggregate. Aggregation can only take place in the presence of type D connecting molecules. Binding the analyte E to the type A or type B binding molecules immobilised on the beads inhibits bead aggregation because there are fewer free binding sites for type D connecting molecules. The higher the concentration of E, the lower the degree of aggregation of the beads.

Figure 4:
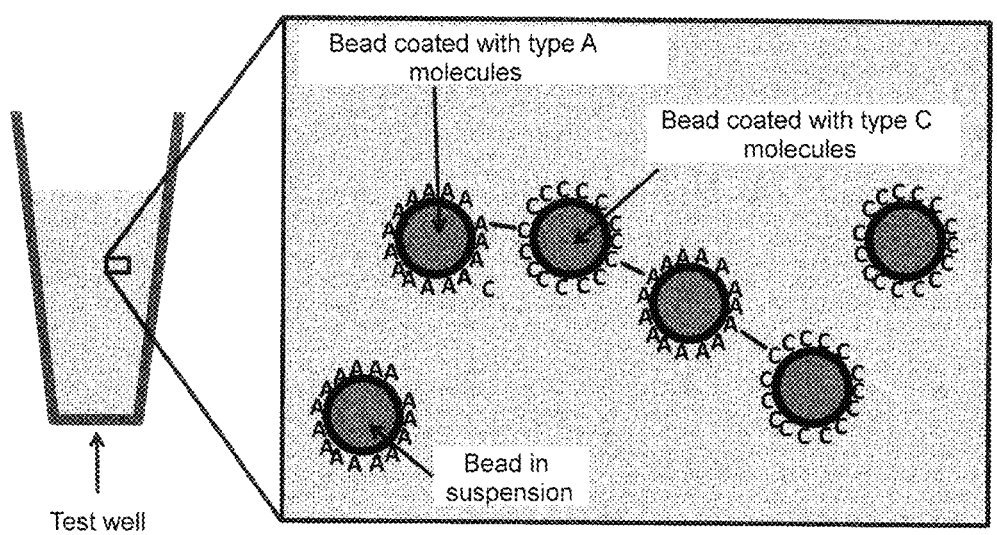
FIG. 4 illustrates a test format wherein beads coated with type A molecules and beads coated with type B molecules form aggregates. Aggregation is inhibited by free type C molecules.

In an additional embodiment, the analyte or an analyte analogue can be immobilised on the bead itself. This embodiment is shown in FIG. 4. In this case, there are beads coated with the binding molecule A and beads coated with the analyte C or an analogue thereof. Preferably, homogenous bead suspensions containing type A and type C beads are first produced, the concentrations of the two bead suspensions having been advantageously optimised beforehand. The type C beads and a sample fluid, which contains the analyte C at a concentration c to be detected, are then preferably introduced into a test well. Aggregation can take place once type A beads have been added, the degree of aggregation reducing as the concentration of the analyte C increases.

Figure 5:
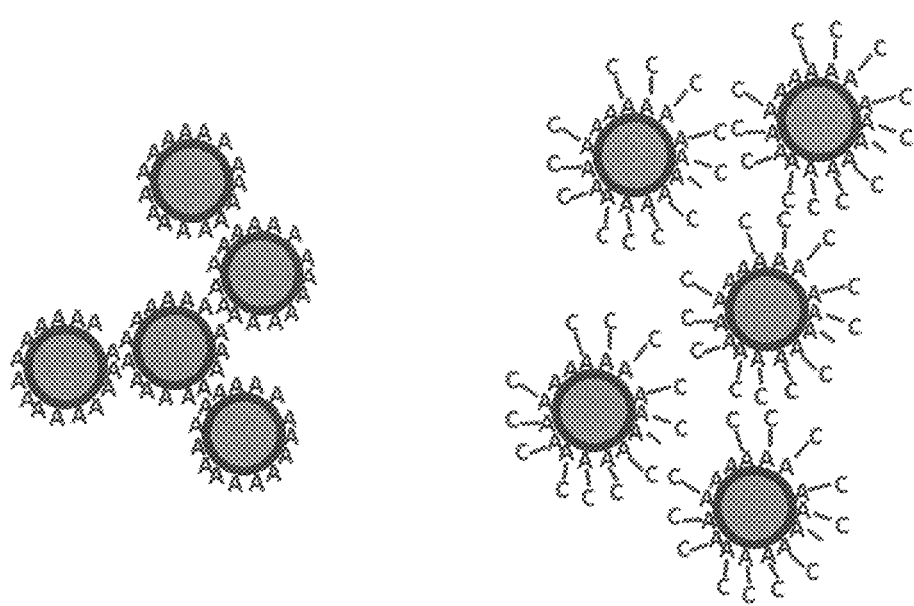
FIG. 5 illustrates a test format utilizing self-aggregation effect to determine the concentration of an analyte.

In an additional embodiment, the non-specific self-aggregation effect can be used to determine the concentration of the analyte. This embodiment is shown in FIG. 5. The beads in this case are beads coated with type A binding molecules. There is a tendency for self-aggregation (left). When analyte molecules C having one single binding site for the binding molecule A are added, self-aggregation is inhibited because the distance between the individual beads is greater. As the concentration of the analyte C increases, the degree of aggregation drops (right).

In an additional embodiment, there are two different bead types in suspension: magnetisable beads on one hand, which are coated with type A molecules, and non-magnetisable beads on the other hand, which are coated with type B molecules. The non-magnetisable beads can, for example, consist of polymer material (e.g. polystyrene), starch, silane, etc., preferably of polymer material, in particular polystyrene.

Figure 13:
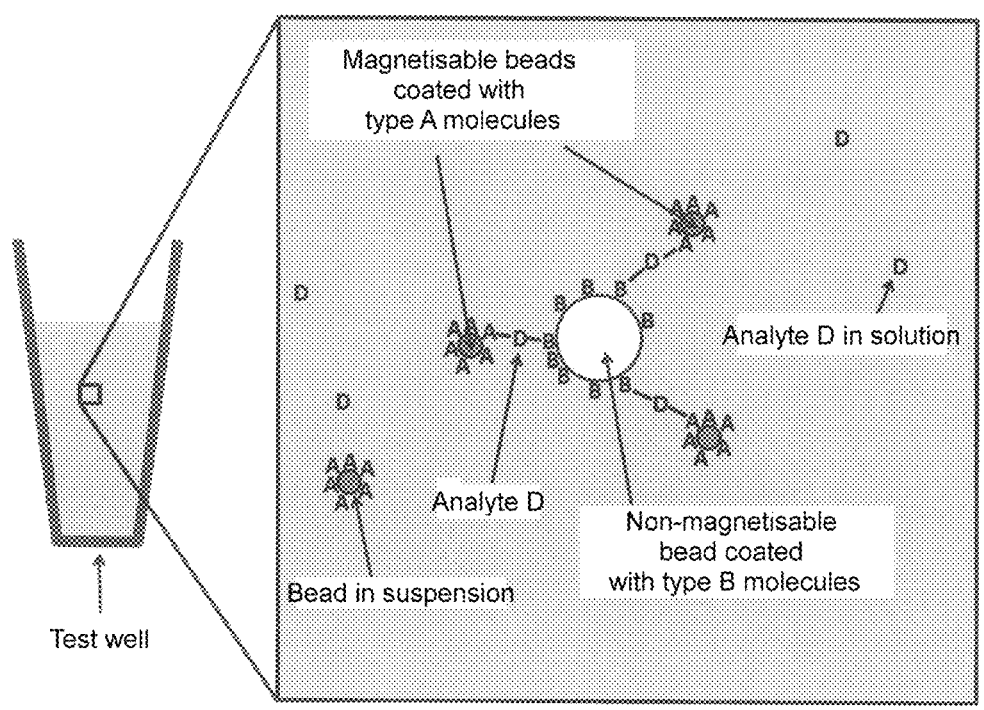
FIG. 13 illustrates a test format wherein type D analyte molecules to be detected establish a connection between non-magnetisable and magnetisable beads.

Type D analyte molecules to be detected establish a connection between non-magnetisable and magnetisable beads. The higher the concentration c of the analyte D, the more magnetisable beads bind to non-magnetisable beads. The principle is illustrated in FIG. 13.

In the variant having two different magnetisable and non-magnetisable bead types, the concentration of the analyte can be determined by means of the speed at which the bead layer forms. If the magnetisable beads are bound to non-magnetisable beads, they move more slowly in the magnetic field.

Figure 14:
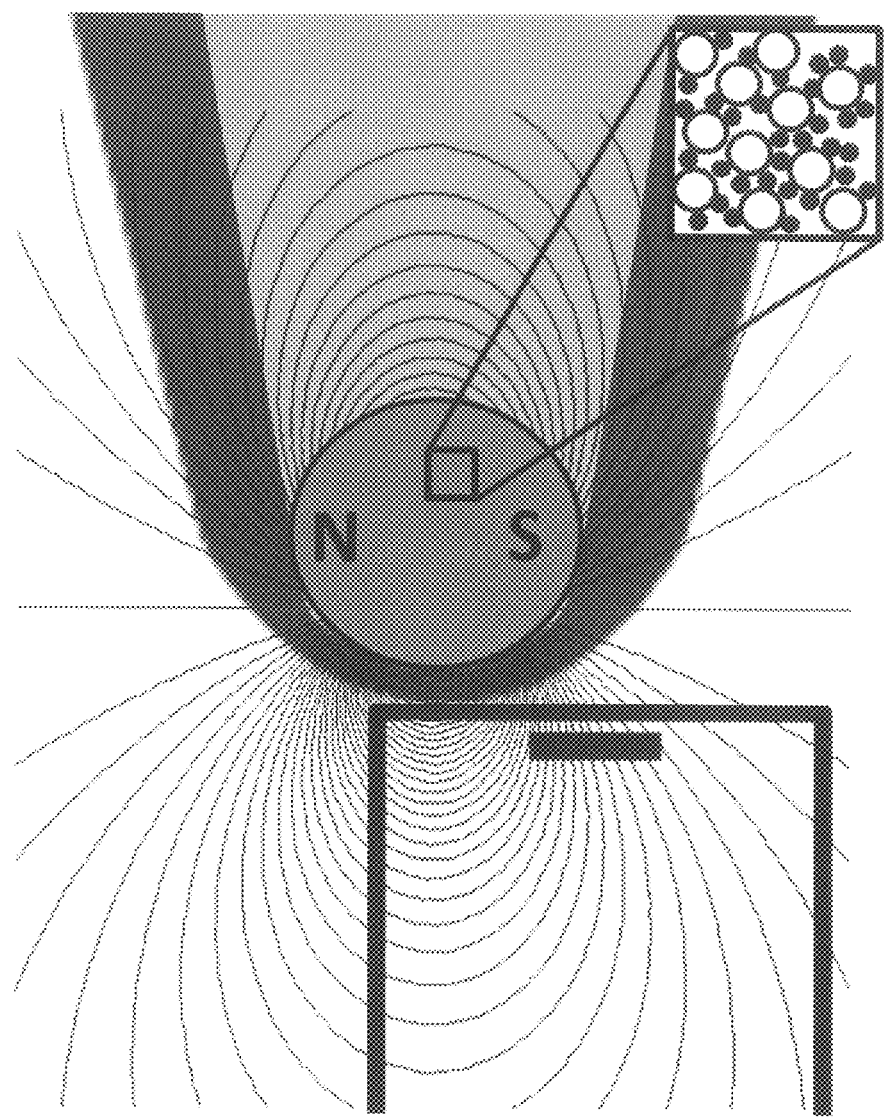
FIG. 14 illustrates a test format for detecting analyte concentration by measuring the absolute magnetic field strength in an embodiment wherein magnetisable beads are bound to non-magnetisable beads.
Figure 15:
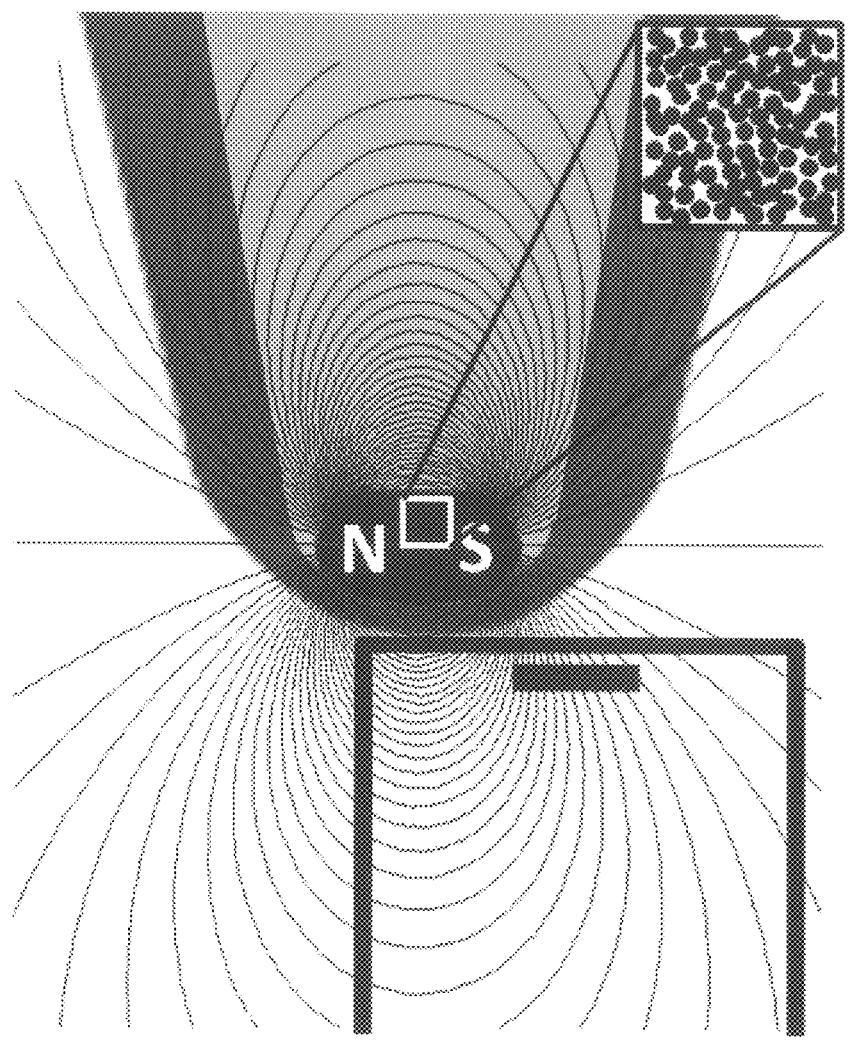
FIG. 15 illustrates a test format for detecting analyte concentration by measuring the absolute magnetic field strength in an embodiment wherein there are no bonds between magnetisable beads and non-magnetisable beads.

In the embodiment having two different magnetisable and non-magnetisable bead types, the analyte concentration can also be determined by measuring the absolute magnetic field strength after a particular point in time or after particular points in time. It can be determined therefrom how many magnetisable beads are bound to non-magnetisable beads. If there are many such bonds, the density of the magnetisable beads in the bead layer is lower, as a result of which the magnetic signal is smaller (see FIG. 14). If no such bonds exist, the density of the magnetisable beads in the bead layer is greater, and the magnetic signal is thus larger (see FIG. 15). Appropriate grading is possible. In short, the more analyte molecules present in the bead suspension, the lower the density of the magnetic beads in the layer and the smaller the magnetic signal.

The embodiment having two different magnetisable and non-magnetisable bead types is also suitable for separating bound and unbound beads. The non-magnetisable beads can consist of a material having a low density that is slightly above that of water ($\rho$: 1.01-2.59 $g/cm^3$). If the fluid density is then increased above the density of the non-magnetisable beads (e.g. by adding sucrose, polysucrose (e.g. Ficoll), glycerol, various polyols, etc.), the beads float to the surface. If the buoyancy is strong enough, the non-magnetisable beads also float to the surface when magnetisable beads have bound thereto. It is possible to wait for the beads to float to the surface before introducing the measurement well into the magnetic field. In this case, they are then too high up to be pulled back down by the magnetic field, which is too weak at this point. Even without waiting, some of the beads are located outside of the range of the magnetic field. In this way, unbound beads can be separated from bound beads. The higher the analyte concentration, the smaller the magnetic signal.

Instead of non-magnetisable beads, use can also be made of polymer molecules which are functionalised with type B molecules. If analyte molecules are present, said type B molecules then cause aggregation between the magnetisable beads. It is in turn possible to determine the analyte concentration by means of a kinetic measurement.

The polymer molecule can, for example, be a synthetic or natural polymer, for example starch (derivatives), dextrane (derivatives), polyethylene glycol, polyacrylamide, etc.

The various embodiments of the detection system according to the invention are distinguished in that the degree of aggregation of the beads varies depending on the presence and/or the concentration in the sample of the analyte to be detected.

Preferably, the detection is carried out in a test well, into which the sample fluid and the magnetisable beads have been introduced, preferably as a suspension. In addition, buffers and/or additional reagents may optionally be present. The volume of the test well is preferably from 1-1000 μl, more preferably from 50-300 μl. Depending on the test format, said well can be in different shapes. It preferably has an elongate shape, e.g. having a length of from 3 mm to 50 mm, in order to resolve the differences in speed between nanobeads and nanobead aggregates in an effective manner and to save on fluid volume.

Step (b) of the method according to the invention comprises determining the degree of aggregation of the magnetisable beads by magnetic detection. In this context, step (b) preferably comprises generating a magnetic field in the test well that causes the magnetisable beads to move. More preferably, the detection of the degree of aggregation of the beads comprises determining the movement of the magnetisable beads in a non-homogenous magnetic field.

The detection of the analyte in the sample is based on the fact that cross-linked bead aggregates move at a different speed from individual beads in a magnetic field. Preferably, the movement takes place in a magnetic field gradient in the direction of the increasing magnetic field strength. Moreover, large cross-linked bead aggregates move at a different speed, e.g. in the direction of the increasing magnetic field strength, from small cross-linked bead aggregates.

Therefore, beads or bead aggregates migrate out of the suspension towards the points in the measurement well where the applied magnetic field $\vec{B}_1(\vec{r})$ is strongest and accumulate there, and specifically at a speed that is dependent on the degree of cross-linkage between the beads.

The force acting on the beads is preferably the result of a field gradient in the magnetic field. The field gradient can be generated by a non-homogenous magnetic field in which the beads are then accelerated in the direction of the increasing magnetic field strength.

Since the beads are magnetised in the external magnetic field $\vec{B}_1(\vec{r})$, they in turn generate a magnetic field which leads to a time-dependent additional field $\Delta\vec{B}(c, t, \vec{r})$ which is superimposed on the external field $\vec{B}_1(\vec{r})$. This time-dependent change is measured ("kinetic measurement"). The development over time of the additional field is dependent on the degree of aggregation or cross-linkage of the beads and thus on the concentration of the analyte.

Advantageously, beads having as high a saturation magnetisation as possible are used to generate both an additional field that is as large as possible and accordingly a strong signal for detection.

Preferably, the analyte determination by means of the method according to the invention includes a system calibration, the degree of aggregation or cross-linkage of the beads being determined in control samples either not containing an analyte or containing one or more known analyte concentrations. To calibrate the system, mixtures are preferably made of bead suspensions and sample fluids containing the analyte at fixed concentrations $c_i$. Using these mixtures, kinetic curves $\Delta\vec{B}(c_i, t, \vec{r})$ and $|\Delta\vec{B}(c_i, t, \vec{r})|$ are recorded, $\vec{r}_0$ being the position of the magnetic field sensor. The parameters defining the shape of the kinetic curves are measured or determined by means of a curve fit.

In many cases, a part of the kinetic curve can be described by a function of the shape $$|\vec{B}_{Fit}(t)| = P + Q \cdot \left(1 - e^{-\frac{t}{\tau(c)}}\right). \quad (1)$$

The time constant $\tau(c)$ is dependent on the concentration and is determined by experiment (establishing the so called "standard curve"). The standard curve is created by an additional curve fit to the discrete measured value $\tau_i(c)$.

An additional important kinetics follows the Langmuir equation $$|\vec{B}_{Fit}(t)| = P \cdot \frac{t/\tau(c)}{1 + t/\tau(c)} \quad (2)$$

Other kinetic curves are also conceivable, which for example can be fitted by means of a polynomial function.

If sample fluid is now present together with an unknown concentration cx of the analyte, a kinetic curve is first recorded, which is fitted using a curve fit according to equation (1) or optionally equation (2). By means of the time constants determined in this manner, the concentration $c_x$ is calculated by means of the assignment function $c \rightarrow \tau(c)$ or $\tau \rightarrow c(\tau)$.

In certain embodiments of the method, the detection of the degree of aggregation can include the use of a test well having a filter element, e.g. a sieve. In this case, the filter element is more permeable to non-aggregated beads than to bead aggregates. The diameter of the holes in the filter element can for example be in the range of from approximately 100 nm to approximately 10 μm.

Using a filter element allows differences in the speeds of individual beads, relatively small bead aggregates and relatively large bead aggregates to additionally be increased. Above a certain size, the aggregates are retained completely by the filter element, and therefore the absolute magnetic signal S in the saturation of the kinetics is then also reduced. S can therefore also be used as an amount for the concentration of an analyte. S corresponds to $|B_{Fit}|$ after a sufficiently long time t. A standard curve S(c) can thus be created in a similar manner to the preceding section. The presence and the concentration of an analyte can be determined as described above.

To prevent the holes in the filter element from becoming too clogged with bead aggregates, the test well can be moved mechanically or by means of ultrasound stimulation.

Figure 6:
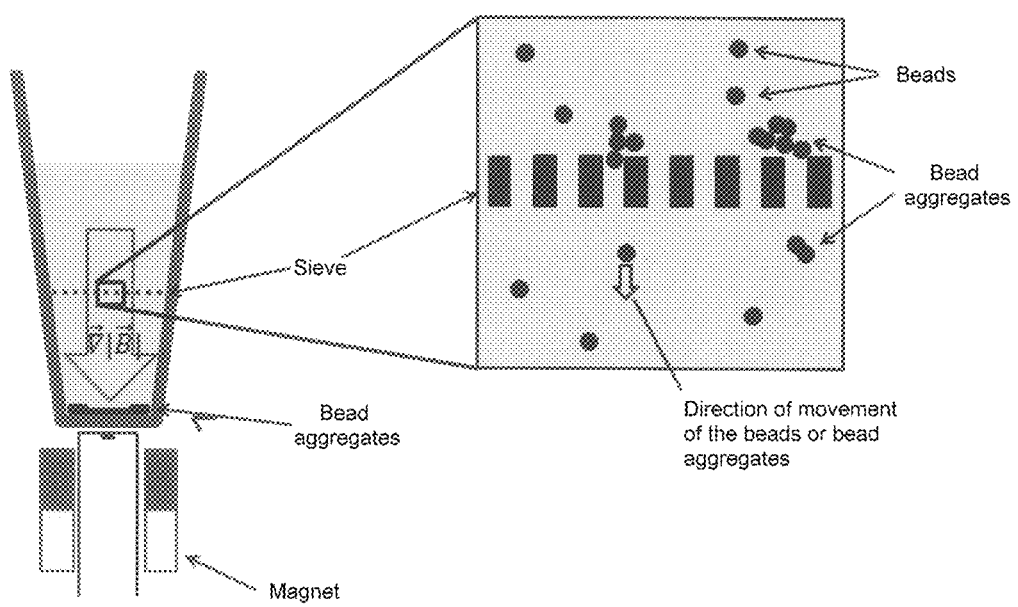
FIG. 6 shows a test well having an integrated sieve wherein individual beads can pass substantially unhindered through the sieve but bead aggregates migrate more slowly through the sieve or cannot pass through the sieve at all above a certain size.

FIG. 6 shows a test well having an integrated sieve. A magnetic field is generated in the test well by a magnet. In the left-hand portion of the figure, the increasing field strength is denoted by the arrow $\vec{\nabla}|\vec{B}|$. As described above, the beads migrate in the direction of the increasing magnetic field strength. In this case, individual beads can pass substantially unhindered through the sieve, whereas bead aggregates migrate more slowly through the sieve or cannot pass through the sieve at all above a certain size. In the right-hand portion of FIG. 6, the direction of movement of a bead is indicated by way of example.

To measure the magnetic field or changes in the magnetic field, a magnetic field sensor is used. Hall sensors or magnetoresistive sensors are examples of suitable sensors.

Instead of a magnetic field sensor, a different sensor can also be used to detect the bead layer. The impedance and inductance of a coil or coil arrangement below the bead layer are examples of possible measured variables.

In principle, it is advantageous to position the magnetic field sensor as closely as possible to the bead aggregates and to magnetise the beads as strongly as possible.

There exist magnetic field sensors which can be used to measure extremely small fields. At a distance of up to a few millimetres, the influence on the field by the bead aggregates is in the nano and microtesla range.

To measure the change in the magnetic field that is dependent on the degree of aggregation of the beads, it may be preferable to use an annular magnet, in particular a ring magnet having zero-field points. The ring magnet having zero-field points can be either a permanent magnet or an electromagnet.

There are two points around a ring magnet at which the magnetic field is zero (zero-field points). The magnetic field sensor is preferably positioned in the region of the upper zero-field point. The test well can be arranged above the zero-field point, preferably directly above the zero-field point. The described bead aggregates that are detected by the probe now accumulate at the bottom of the well. This embodiment is shown in FIGS. 7 and 8.

Figure 7:
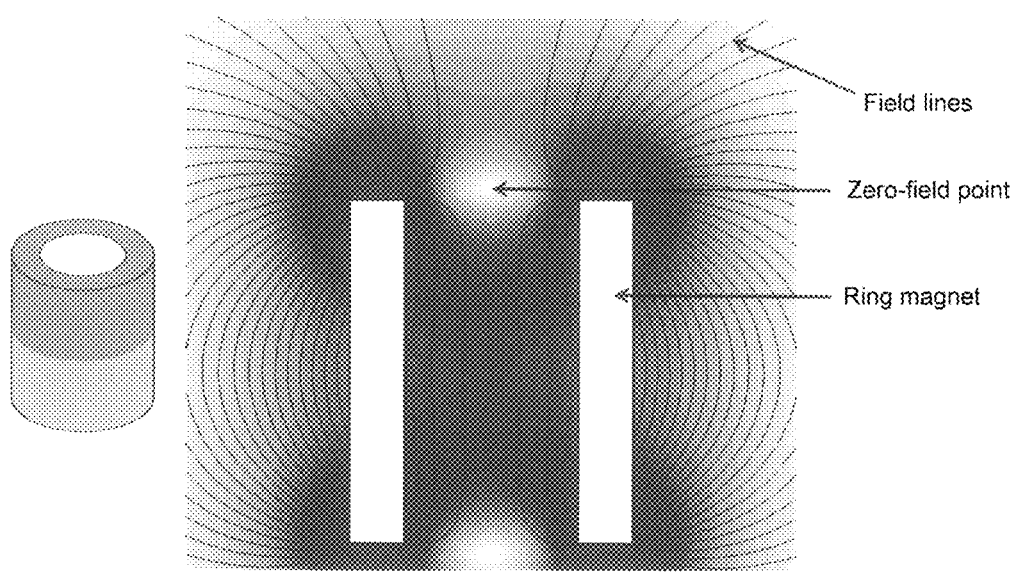
FIG. 7 shows the field distribution around a ring magnet.

FIG. 7 shows the field distribution around a ring magnet. The ring magnet is shown in cross section in the large image. The darker the grey, the greater the strength of the magnetic field.

Figure 8:
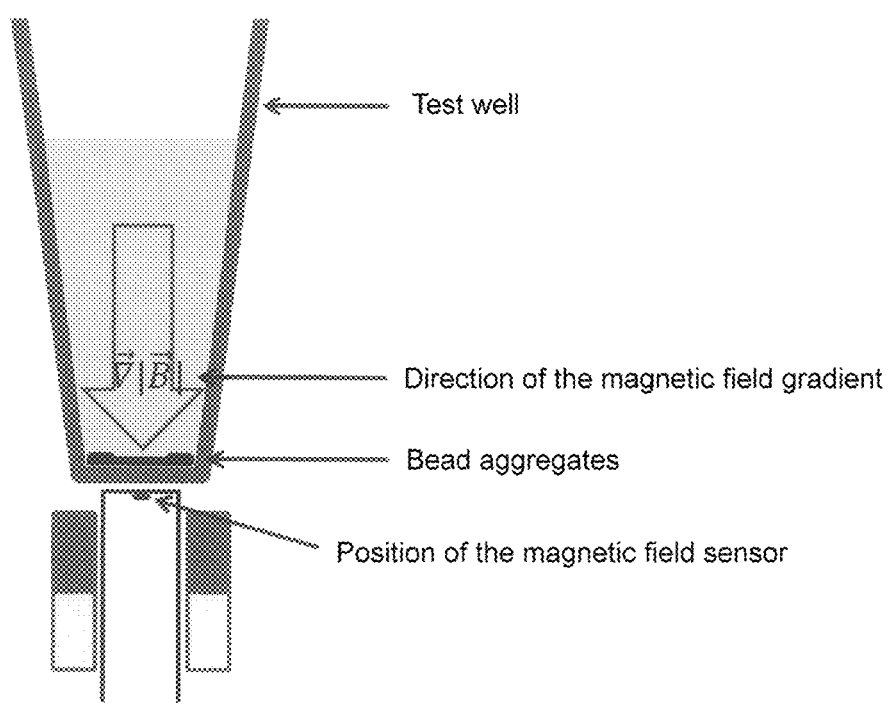
FIG. 8 shows a measurement arrangement comprising ring magnets.

FIG. 8 shows the arrangement of a measurement arrangement comprising ring magnets. In this case, a magnetic field is generated in a test well, the direction of the magnetic field gradient being indicated by the arrow $\vec{\nabla}|\vec{B}|$. The position of the active region of the magnetic field probe coincides with the upper zero-field point. The beads or bead aggregates migrate in the test well in the direction of the magnetic field gradient, i.e. in the direction of the arrow. Owing to the annular shape of the magnet, the beads preferably accumulate in an annular manner at the bottom of the test well, the reason being that the magnetic field is stronger here than in the centre. Advantageously, use can thus be made of a test well having an at least partly flat bottom. This effect only disappears when the well is at a certain distance from the magnet, and a uniform bead layer forms at the bottom (see distribution of the field strength in FIG. 7).

In another preferred embodiment, the magnetic field can be generated by an electromagnet which functions intermittently. In the simplest case, the electromagnet consists of a cylindrical coil, to which, depending on the required field strength, metal components can be attached in order to increase the field strength.

Figure 9:
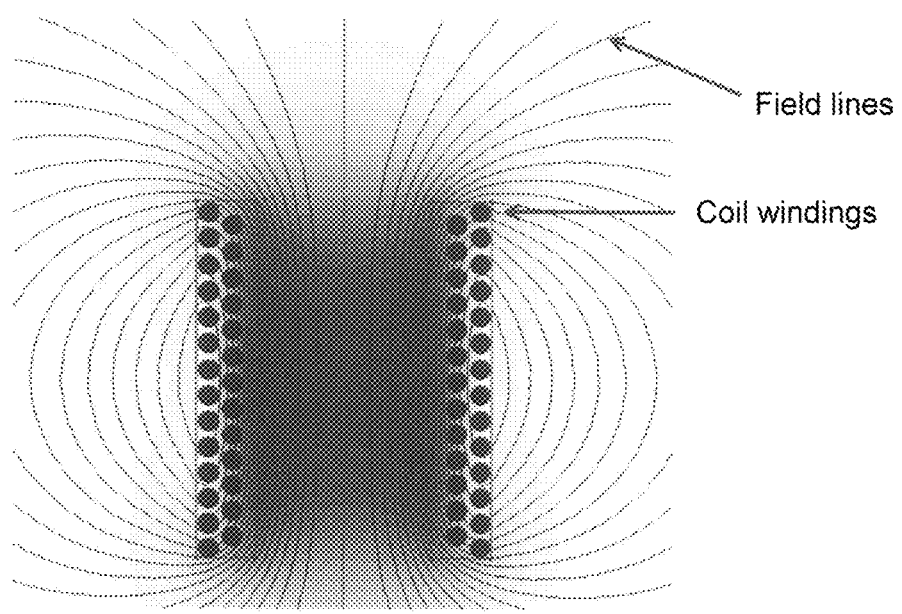
FIG. 9 shows the field distribution around an electromagnet formed as a coil.

FIG. 9 shows the field distribution around an electromagnet formed as a coil. The coil can be positioned below the test well, optionally together with field-strengthening metal components.

Figure 10:
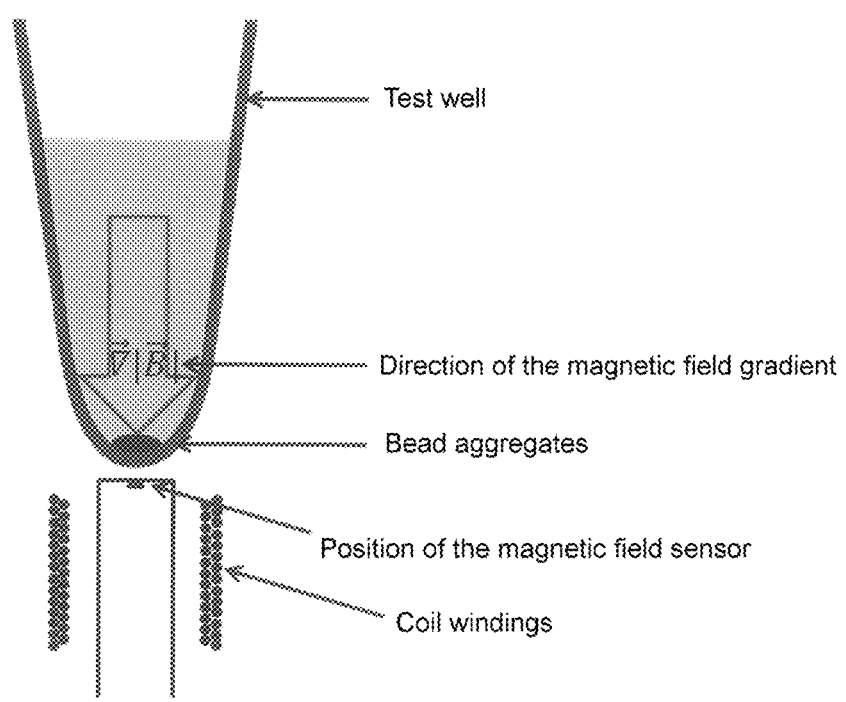
FIG. 10 shows a measurement arrangement comprising an electromagnet.

FIG. 10 shows the arrangement of such a measurement arrangement comprising an electromagnet. A magnetic field is generated in the test well by the electromagnet. The direction of the magnetic field gradient is shown by the arrow $\vec{\nabla}|\vec{B}|$. The beads or bead aggregates migrate in the test well in the direction of the magnetic field gradient and accumulate at the bottom of the test well. By comparison with the variant having a ring magnet (see FIG. 7), in this case more beads also accumulate in the middle at the bottom. Therefore, it may be advantageous to use a vessel that tapers conically downwards.

In order to measure with a greater level of sensitivity, the electromagnet can be deactivated at defined intervals $\Delta t$ for a given time period $\delta t$. The residual magnetisation of the bead aggregates is then measured by the sensor. In a similar manner to the ring magnet variant, a kinetic curve is thus recorded and can be used to draw conclusions on the speed at which the bead aggregates form.

Figure 11:
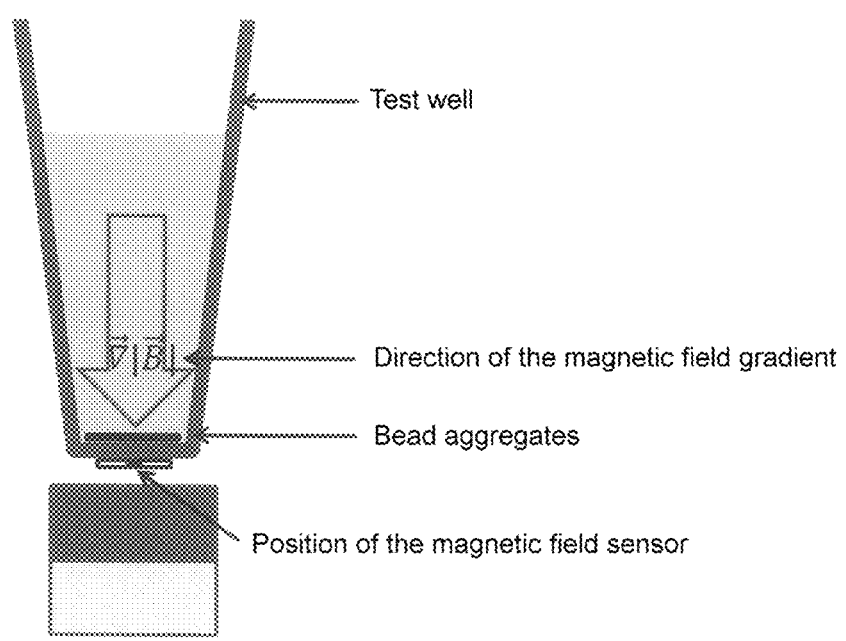
FIG. 11 shows a measurement arrangement using permanent magnets that produce different field geometries.

Other embodiments comprising permanent magnets or electromagnets that produce different field geometries are also conceivable. It may thus be possible in certain cases to use a permanent magnet or an electromagnet which does not have any zero-field points and to not switch said magnet off during measurement (see FIG. 11). It is also conceivable, for example, to use a very small total field $\vec{B}_1(\vec{r})$.

Figure 16:
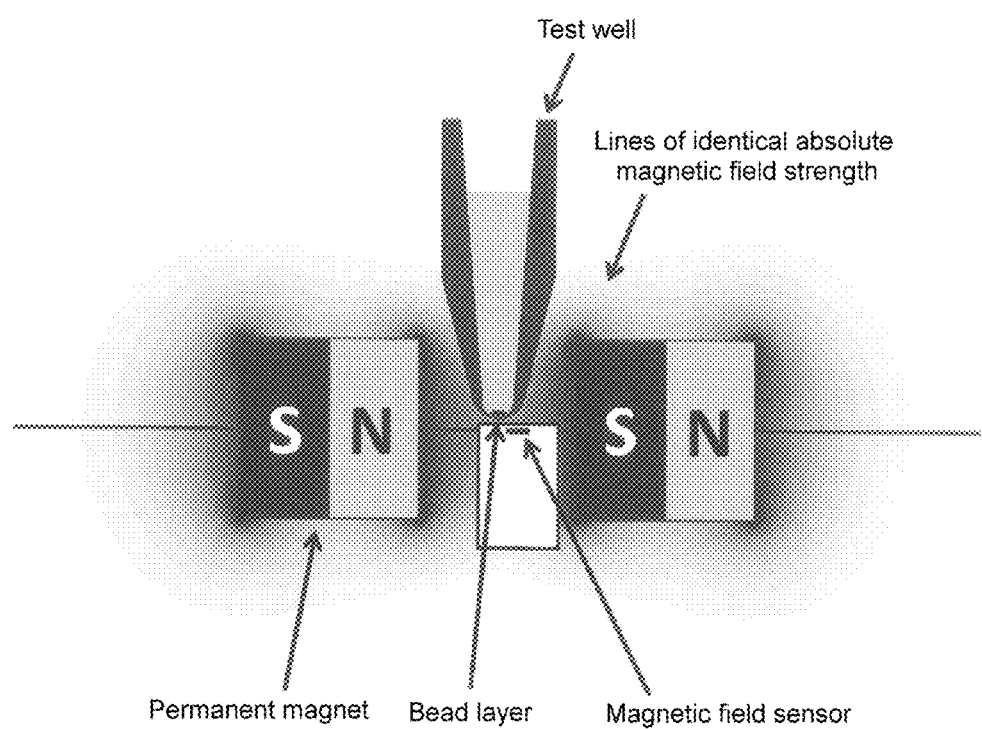
FIG. 16 shows an arrangement wherein a test well is located in a strong stationary magnetic field which primarily extends in the horizontal direction and the strength of which increases downwards. The magnetic field is generated by two permanent magnets which are positioned on either side of the test well.

FIG. 16 shows an embodiment in which the test well is located in a strong, stationary magnetic field, which primarily extends in the horizontal direction and the strength of which increases downwards. Such a field can be generated by two permanent magnets which are positioned on either side of the test well (FIG. 16).

In this magnetic field geometry, the magnetisable beads are again accelerated downwards so that a layer of beads or bead aggregates is formed. The beads are magnetised in the direction of the field lines of the external magnetic field and thus generate an additional magnetic field.

Figure 17:
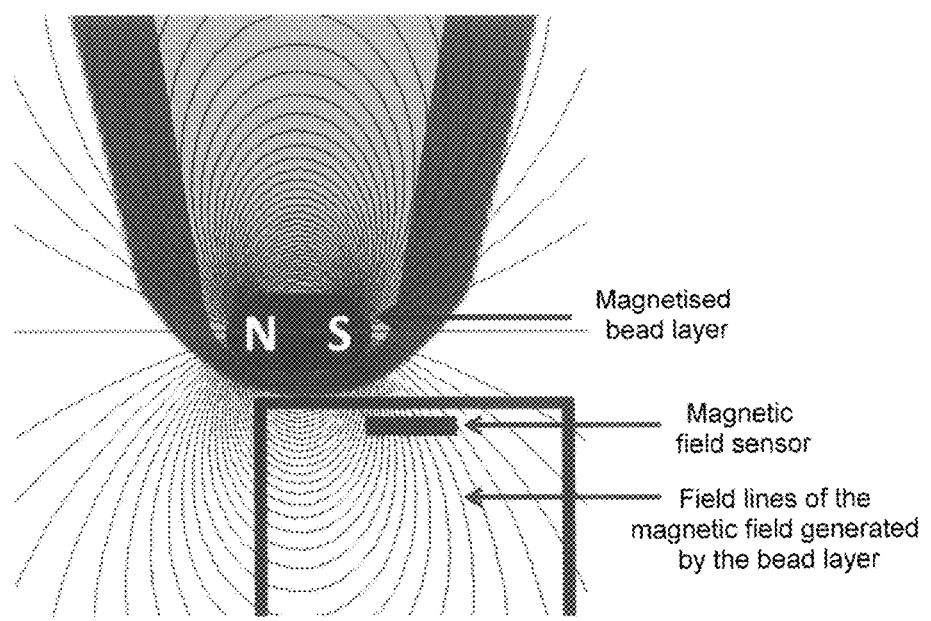
FIG. 17 illustrates positioning of a magnetic field sensor not centrally below the test well but off-set in the N-S direction.

The magnetic field sensor is positioned below the test well such that the vertical component of the magnetic field generated by the bead layer can be measured. For this purpose, said sensor is not positioned centrally below the test well, but rather so as to be offset in the N-S direction (see FIG. 17). The test well, on the other hand, is located centrally between the two permanent magnets so that the beads accumulate as far down as possible.

Preferably, the bead aggregates accumulate and are measured at the bottom of the measurement well, although this can also take place at a side of the measurement well. Optionally, the test wells can be stimulated by ultrasound in order to manipulate the speed at which the bead aggregates accumulate.

One embodiment, in which two different bead types are present in suspension, specifically magnetisable beads coated with type A molecules and non-magnetisable beads coated with type B molecules, can be used to separate analyte-bound beads from unbound beads. The present invention thus also provides a method for separating off an analyte, comprising the steps of (i) providing a suspension comprising magnetisable beads coated with a first type of binding molecules, non-magnetisable beads coated with a second type of binding molecules, and at least one suspension medium, the density of the non-magnetisable beads $\rho_{nmB}$ being in the range of from 1.01-2.5 g/cm³, preferably from 1.1-2.5 g/cm³, (ii) adding analyte to the suspension, (iii) adjusting the density of the suspension medium to a value of $\rho_{Medium} > \rho_{nmB}$, (iv) separating off the beads bound to the analyte. In a preferred embodiment, the suspension medium is water.

By adjusting the density of the suspension medium to be above that of the non-magnetisable beads, e.g. by adding sucrose, polysucrose, e.g. Ficoll, glycerol, polyol, etc., the beads float to the surface. If the buoyancy is strong enough, the non-magnetisable beads also float to the surface if magnetisable beads have bound thereto. It is thus possible to separate off the analyte-bound beads from the unbound beads in a simple manner. The embodiment can also be used to determine the analyte concentration. For this purpose, the separated sample is introduced into the measurement well and into the magnetic field. The analyte-bound beads are located at the surface and cannot be pulled downwards by the magnetic field, since said field is too weak. The higher the concentration of analyte, the lower the magnetic signal.

A reagent containing one or more species of magnetisable beads is suitable for carrying out the method according to the invention. The beads are coated with binding molecules, as described above, so that the magnetisable beads can aggregate, in a manner detectable by magnetic detection, depending on the presence and/or concentration of the analyte in the sample. In addition, the reagent also contains additional components, e.g. binding molecules or cross-linking molecules in a free state, and additives, e.g. buffers, anti-interference reagents, etc.

As described above, the reagent can contain other control samples as additional constituents for calibrating the detection system.

A suitable device for carrying out the method according to the invention comprises a test well, a magnet for generating a magnetic field, in particular a non-homogenous magnetic field or a magnetic field gradient, in the test well, and a magnetic sensor suitable for measuring changes over time in the magnetic field in the test well.

The device can also contain a unit for analysing the signals measured by the sensor, e.g. a processor, and optionally a housing, a control panel, etc.

The following examples explain the present invention.

EXAMPLE 1

Functionalised beads from TurboBeads (www.turbobeads.com) were used. The beads consist of cobalt and have a saturation magnetisation of approximately 158 emu/g. The diameter is approximately 30 nm. The cobalt beads are covered with a carbon layer.

For this test, use was made of beads in which the carbon layer is functionalised with biotin molecules. Streptavidin was used as the test analyte. Streptavidin has four binding sites for biotin. The test system thus implemented corresponds to the first described embodiment (see FIG. 1).

The Teslameter FH 54 comprising the Hall probe HS-AGES-4805 from MAGNET-PHYSIK (www.magnet-physik.de) was used to measure the magnetic field strength.

Figure 12:
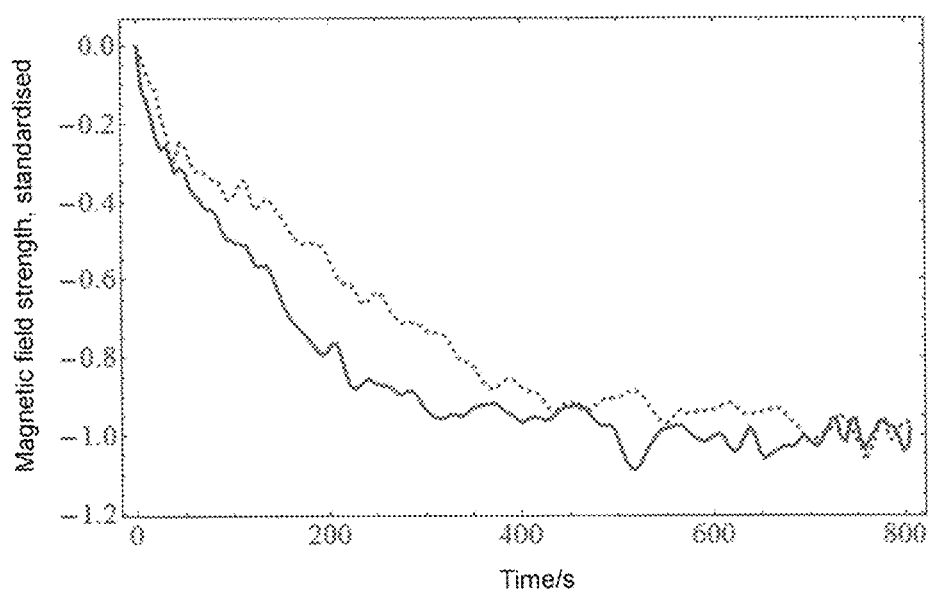
FIG. 12 shows the magnetic field strength recorded in Example 1.

The configuration of FIG. 8 was used as the experimental arrangement, though with a test well that tapers downwards. FIG. 12 shows the time-dependent change in the magnetic field strength at the location of the magnetic field sensor.

At the start of the measurement, there were 500 µl of homogenous nanobead suspension in the measurement well. The concentration of the nanobeads was $2.67 \cdot 10^{11}$ nanobeads/ml; the binding capacity was 0.1 mmol/g.

Since there was a permanent magnet below the test well, the beads began migrating downwards as soon as the suspension was added. The measured magnetic field strength is shown as a continuous black line in FIG. 12.

In another experiment, the same process was carried out, the only difference being that the bead suspension was mixed with a streptavidin solution prior to being added. Streptavidin forms a bond with biotin such that a streptavidin layer forms on the surface of the beads. Since streptavidin has four biotin binding sites, the nanobeads aggregate (see FIG. 1). The streptavidin concentration in the bead suspension was 333 pmol/ml.

The recorded magnetic field strength is shown as a dashed curve in FIG. 12.

It can be clearly seen that the nanobeads or nanobead aggregates have slower kinetics in the experiment with streptavidin than in the experiment without streptavidin.

This effect could be reproduced.

EXAMPLE 2

Detecting an Analyte Having a Plurality of Binding Sites to Binding Molecules (See FIG. 1)

Use was made of an arrangement in which the beads are introduced into a field running horizontally (see FIG. 16).

The Teslameter FH 54 comprising the Hall probe HS-AGES-4805 from MAGNET-PHYSIK (www.magnet-physik.de) was used to measure the magnetic field strength.

Magnetisable beads from Merck Millipore (Estapor brand, www.estapor.com) having a diameter of approximately 170 nm were used. The beads consist of a polystyrene matrix in which magnetite particles are embedded. The surface of the beads was functionalised with biotin.

The total amount of fluid was constant at 100 µl. The concentration of the magnetisable beads was $1.3 \cdot 10^{12}$ beads/ml.

A reference measurement was taken, in which no streptavidin was admixed. Next, measurements were taken using different streptavidin concentrations. Streptavidin forms a bond with biotin. Since streptavidin has four biotin binding sites, the beads aggregate.

Figure 18:
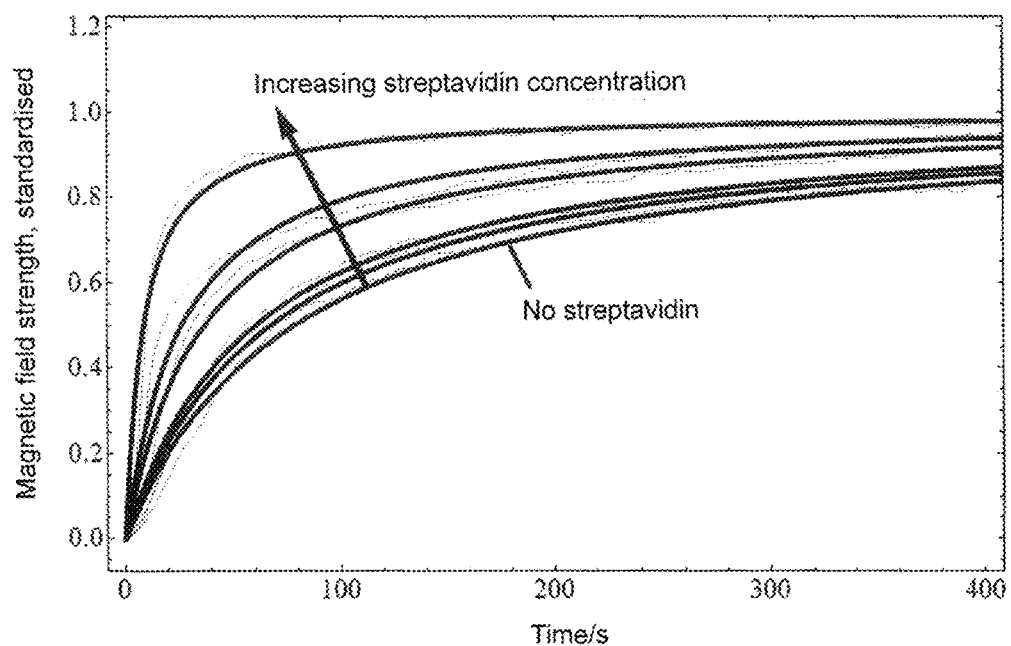
FIG. 18 shows the magnetic field strength measured in Example 2, dependent on the concentration of streptavidin.

The results are shown in FIG. 18:

The streptavidin concentration increases in the direction of the arrow as follows: no streptavidin; 41.67 nmol/ml; 83.33 nmol/ml; 208.33 nmol/ml; 333.33 nmol/ml; 500 nmol/ml.

The original curves are shown in grey. Fitted curves are shown superimposed thereon in black. Use was made of the Langmuir equation $$|\vec{B}_{Fit}(t)| = P \cdot \frac{t/\tau(c)}{1+t/\tau(c)}.$$

The time constants were determined as follows:
$\tau(0 \text{ nmol/ml})=78.38$ s;
$\tau(41.67 \text{ nmol/ml})=67.25$ s;
$\tau(83.33 \text{ nmol/ml})=60.23$ s;
$\tau(208.33 \text{ nmol/ml})=36.49$ s;
$\tau(333.33 \text{ nmol/ml})=26.04$ s;
$\tau(500 \text{ nmol/ml})=8.34$ s.

EXAMPLE 3

Detecting an Analyte Using Magnetisable and Non-Magnetisable Beads

Use was again made of an arrangement in which the beads are introduced into a field running horizontally (see FIG. 16).

The sensor STJ-220 from Micro Magnetics (www.micromagnetics.com) was used to measure the magnetic field strength.

Magnetisable beads from Merck Millipore having a diameter of approximately 170 nm were used again. The surface of the beads was functionalised with the antigen myeloperoxidase (MPO).

Polystyrene beads, also from the Estapor brand from Merck Millipore, were used as the non-magnetisable beads. These had a diameter of approximately 1000 nm. The non-magnetisable beads were functionalised with anti-human IgG.

The total amount of fluid in this case was 130 µl. The concentration of the magnetisable beads was $7.77 \cdot 10^{11}$ beads/ml; the concentration of the non-magnetisable beads was $1.4 \cdot 10^{11}$ beads/ml.

The magnetisable beads were first mixed with the serum to be tested. Where present, anti-MPO antibodies, which were to be detected, bound to the antigens on the surface of the beads. The non-magnetisable beads were then admixed and the anti-human IgGs immobilised thereon bound to antibodies present. The magnetisable beads, which are smaller by comparison, were thus immobilised on the relatively large non-magnetisable beads.

Figure 19:
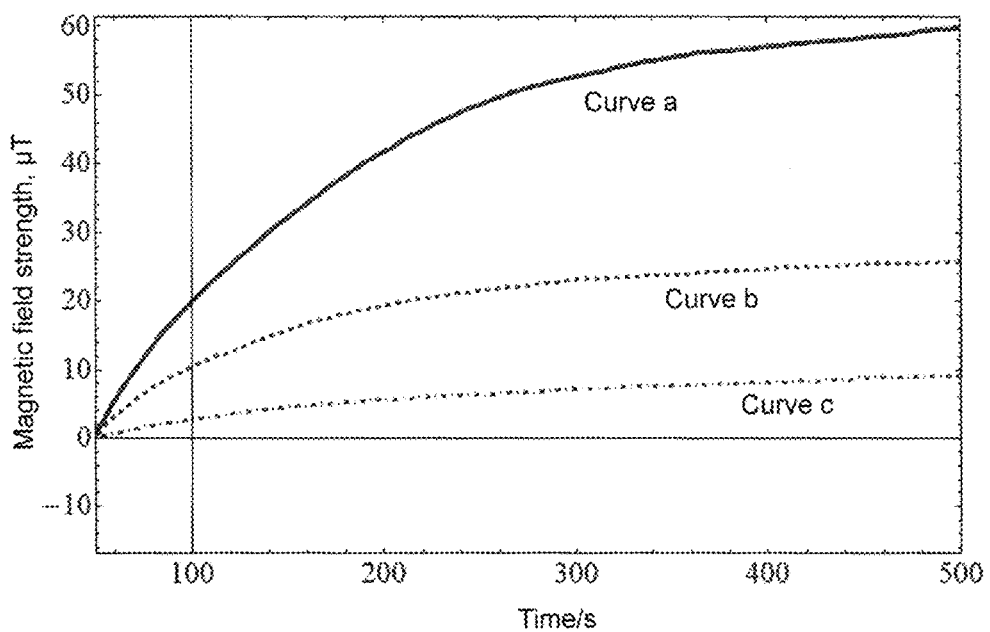
FIG. 19 shows the magnetic field strength measured in Example 3, wherein the continuous line represents measurement without the presence of anti-MPO antibodies, the dash-dot curve represents measurement with a high positive serum and the dotted curve represents measurement with an MPO antibody concentration that is half that of the high-positive serum.

The results are shown in FIG. 19. The continuous line shows a measurement without the presence of anti-MPO antibodies (curve a); the dash-dot curve shows a measurement with a high-positive serum (a very large number of anti-MPO antibodies, curve c); the dotted curve shows a measurement with an MPO antibody concentration that is half that of the high-positive serum (curve b).

In this measurement, the absolute field strength is used to determine the antibody concentration.

Figure 20:
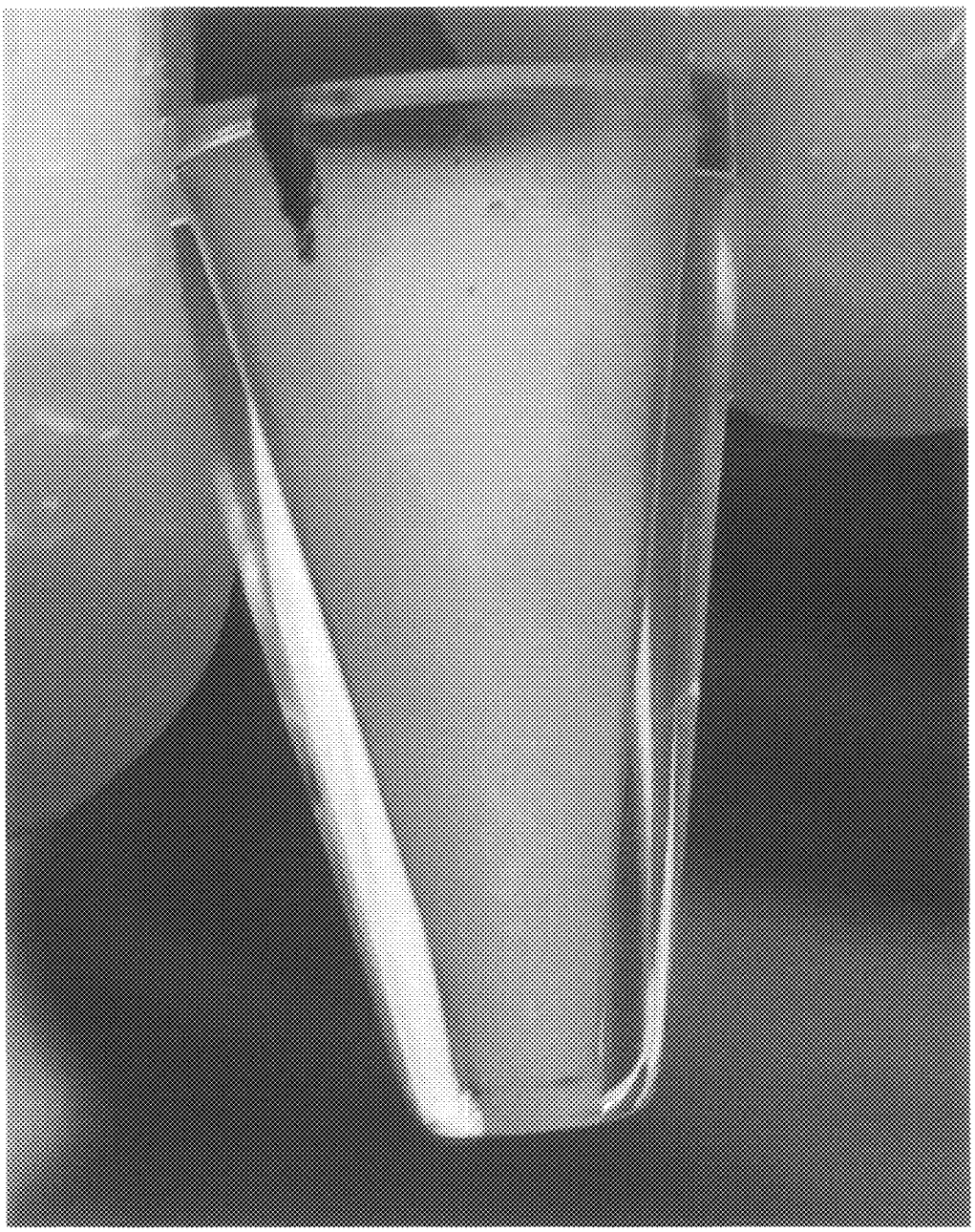
FIG. 20 shows the non-aggregated beads of Example 3.
Figure 21:
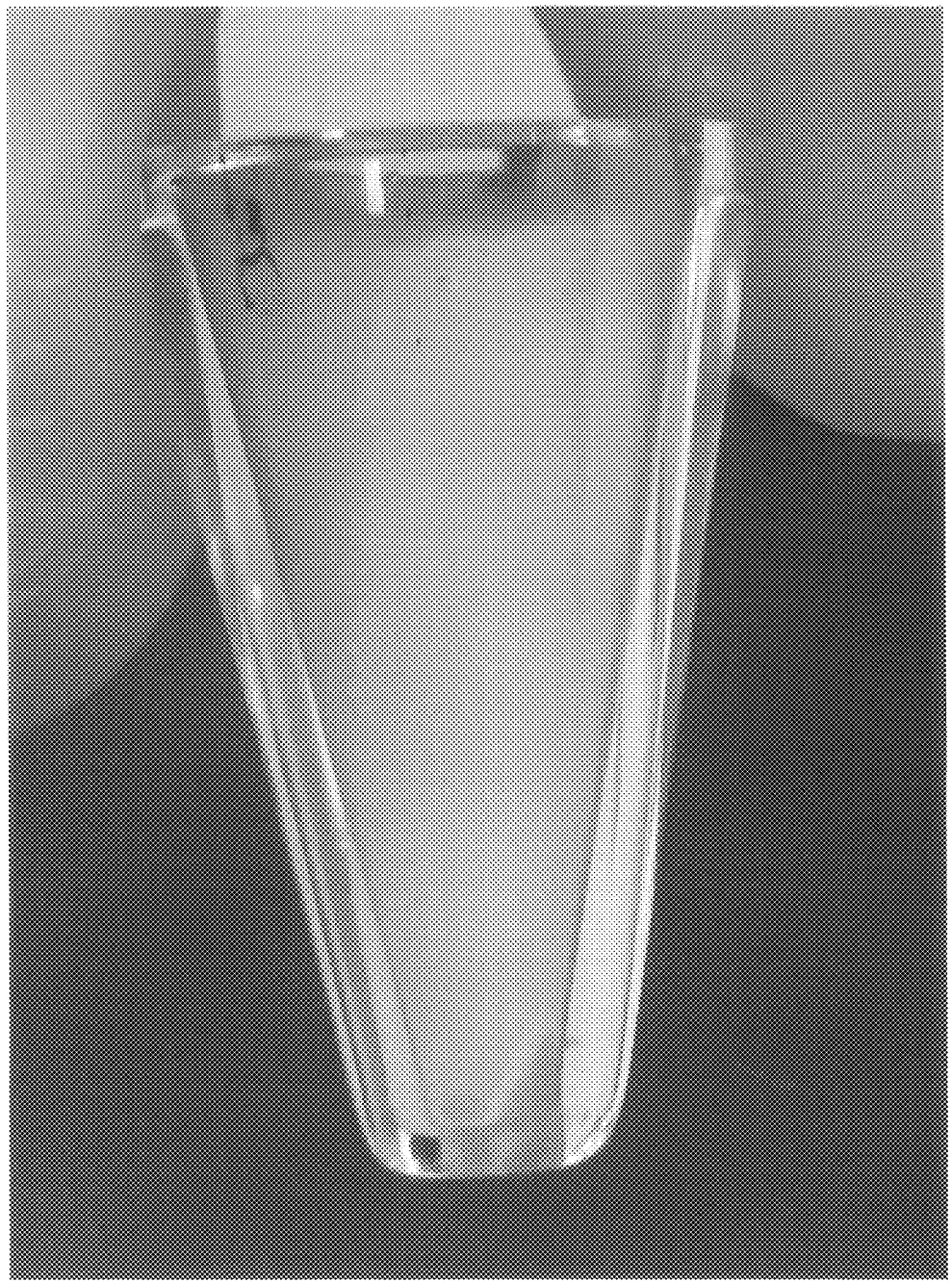
FIG. 21 shows the aggregated beads of Example 3.

FIGS. 20 and 21 respectively show the non-aggregated and aggregated beads.

The invention claimed is:
1. Method for detecting an analyte in a sample, comprising the following steps:
(a) bringing the sample into contact with magnetisable beads and non-magnetisable beads, the beads being coated with binding molecules, wherein the magnetisable beads are coated with type A analyte binding molecules and the non-magnetisable beads are coated with type B analyte binding molecules so that the analyte establishes a connection between the non-magnetisable and the magnetisable beads and the magnetisable beads aggregate depending on the presence and/or concentration of the analyte in the sample, and (b) determining the degree of aggregation of the magnetisable beads by magnetic detection, characterised in that steps (a) and (b) are carried out in a test well, step (b) comprising applying a magnetic field so that the test well is located in a stationary magnetic field which predominantly runs in the horizontal direction and the strength of which increases downwards, whereby the magnetisable beads are caused to move so that a layer of beads or bead aggregates is formed, which beads or bead aggregates are magnetised in the direction of the field lines of the external magnetic field and generate an additional magnetic field which is measured using a magnetic field sensor positioned below the test well, such that the vertical component of the magnetic field generated by the bead layer is measured, the magnetic field sensor not being centrally below a well center of the test well, but rather horizontally offset relative to the well center in a magnetic N-S direction such that the vertical component of the magnetic field generated by the bead layer is stronger than the horizontal component of the magnetic field generated by the bead layer at the horizontally offset magnetic field sensor.

2. Method according to claim 1, characterised in that step (b) comprises applying a magnetic field which causes the magnetisable beads to move.

3. Method according to claim 1, characterised in that a test well is used containing a filtration element which is more permeable to non-aggregated beads than to bead aggregates.

4. Method according to claim 1, characterised in that step (b) comprises applying a magnetic field by using a ring magnet having zero-field points.

5. Method according to claim 1, characterised in that step (b) comprises applying an intermittent magnetic field.

6. Method according to claim 1, wherein the magnetic field sensor is horizontally offset relative to a field center of the stationary magnetic field.

7. Method according to claim 6, wherein the well center is aligned with a field center of the stationary magnetic field.

8. Method according to claim 1, wherein the beads comprise a hydrophilic base coat.

* * * * *